United States Patent
L M et al.

(10) Patent No.: US 11,605,453 B1
(45) Date of Patent: Mar. 14, 2023

(54) APPARATUS, SYSTEMS, AND METHODS FOR DETECTION AND INDEXING CLINICAL IMAGES OF PATIENT ENCOUNTERS

(71) Applicant: ALLSCRIPTS SOFTWARE, LLC, Chicago, IL (US)

(72) Inventors: Shrinathacharya L M, Bangalore (IN); Andrew Robison Burka, Raleigh, NC (US); Georgette Johnson Darnell, Raleigh, NC (US); Jacob Benjamin McGoogan, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

(21) Appl. No.: 16/181,306

(22) Filed: Nov. 5, 2018

(51) Int. Cl.
*G16H 15/00* (2018.01)
*G16H 50/70* (2018.01)
*G16H 10/60* (2018.01)
*G16H 30/20* (2018.01)
*G06F 16/51* (2019.01)
*G06V 10/75* (2022.01)

(52) U.S. Cl.
CPC ............. *G16H 30/20* (2018.01); *G06F 16/51* (2019.01); *G06V 10/751* (2022.01); *G06V 10/758* (2022.01); *G06V 2201/03* (2022.01)

(58) Field of Classification Search
CPC ..... A61B 5/0077; A61B 5/444; A61B 5/7425; A61B 2576/02; A61B 5/0075; A61B 5/1032; A61B 5/1034; G06F 16/245; G06F 16/248; G06F 19/00; G06F 16/51; G16H 10/60; G16H 30/20; G16H 50/20; G16H 15/00; G16H 50/70; G16H 80/00; G16H 40/20; G16H 50/30; G16H 50/50; G16H 10/20; G16H 20/40; G16H 30/40; G06N 3/0454; G06N 7/005; G06N 20/00; G06N 3/08; G06K 9/00288; G06K 2209/05; G06K 2209/27; G06K 9/00469; G06K 9/6267; G06V 10/751; G06V 10/758; G06V 2201/03

See application file for complete search history.

(56) References Cited

U.S. PATENT DOCUMENTS

2014/0378810 A1* 12/2014 Davis .................. A61B 5/0077
                                                        600/407
2016/0140146 A1*  5/2016 Wexler ................... G06F 16/50
                                                        707/741

(Continued)

*Primary Examiner* — Maroun P Kanaan
(74) *Attorney, Agent, or Firm* — Loza & Loza, LLP; Peter Zura

(57) ABSTRACT

Technologies and techniques for managing clinical images in electronic healthcare record systems are disclosed. Disclosed methods and apparatus provide indexing of captured clinical images with minimal or no user input. This is accomplished through providing the ability to set a predetermined type of patient encounter and then retrieving a clinical image of a patient from either an image capture device such as a camera in a mobile device or from a memory device. The methods and systems may also include image recognition of the clinical image to determine the type of the clinical image. Additionally, the indexing is automated, where the automated indexing is based on at least one of the predetermined type of patient encounter and the determined type of clinical image.

8 Claims, 11 Drawing Sheets

(56) References Cited

U.S. PATENT DOCUMENTS

2018/0204111 A1* 7/2018 Zadeh ................. G06K 9/3233
2019/0355455 A1* 11/2019 Mander ................. G16H 15/00
2020/0126648 A1* 4/2020 Schadewaldt .......... G16H 50/70

* cited by examiner

APPARATUS, SYSTEMS, AND METHODS FOR DETECTION AND INDEXING CLINICAL IMAGES OF PATIENT ENCOUNTERS

FIELD OF TECHNOLOGY

The present disclosure is directed to apparatus, systems, and methods for indexing and detecting clinical images. More specifically, the present disclosure is directed to automatic or automated detecting and indexing of clinical images of patient encounters in certain health record systems.

BACKGROUND

Increasingly, healthcare providers utilize digital images of patients taken during patient encounters at a point of care, and such clinical images are stored in electronic health record systems. In particular, when a patient visits a physician or caregiver, clinical images may be captured and indexed according to a particular patient encounter, treatment plan, or diagnosis. These clinical images may be taken using networked camera devices, such as digital cameras within mobile devices, and then stored via a network to the electronic health record system. Depending on the specialty of the caregiver, clinical images may be cataloged, categorized, or indexed differently within the health record system dependent on the specialty. The indexing of clinical images across different caregiver specialties can be inefficient, however, involving many steps including manually selecting types of clinical images being taken when stored and manually indexing these images to be able to correctly store the images within the health record system. Accordingly, the present disclosure is directed to improving the speed and efficiency of clinical image data indexing and image retrieval in electronic health record systems.

SUMMARY

Various apparatus, systems and methods are disclosed herein relating to managing clinical images.

In some illustrative embodiments, a system is disclosed for managing clinical images. The system includes a processing apparatus, a memory operatively coupled to the processing apparatus, the memory configured to store clinical images, and a user interface. The processing apparatus is configured to set a predetermined type of patient encounter, retrieve a clinical image of a patient from one of the user interface or the memory, determine a type of the clinical image, and determine indexing of the clinical image based on at least one of the predetermined type of patient encounter and the determined type of clinical image.

In some other illustrative embodiments, a processor-based method is disclosed for managing clinical images in a processing apparatus. The method includes setting a predetermined type of patient encounter, retrieving a clinical image of a patient from one of the user interface or the memory, determining at type of clinical image, and determining indexing of the clinical image based on at least one of the predetermined type of patient encounter and the determined type of clinical image.

In yet some further illustrative embodiments, an apparatus is disclosed for managing clinical images. The apparatus includes a processing apparatus, a memory operatively coupled to the processing apparatus, where the memory configured to store clinical images and associated indexes for indexing the clinical images in the processing apparatus, and a user interface. Additionally, the processing apparatus is configured to set a predetermined type of patient encounter, retrieve a clinical image of a patient from one of the user interface including a camera device or the memory, determine a type of the clinical image, and determine indexing of the clinical image based on at least one of the predetermined type of patient encounter and the determined type of clinical image.

BRIEF DESCRIPTION OF THE FIGURES

The present invention is illustrated by way of example and not limitation in the figures of the accompanying drawings, in which like reference numbers indicate similar elements and in which.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that the programming techniques and hardware arrangements disclosed herein, which may be embodied on tangible media, are configured to transform the conventional hardware components into new machines that operate more efficiently (e.g., providing greater and/or more robust data, while using less processing overhead and/or power consumption) and/or provide improved user interfaces for human-machine interaction.

It is particularly noted that the present disclosure provides an automatic or automated indexing of clinical images, which may also include automated image recognition, to more efficiently index such images. Furthermore, the present disclosure may also provide for automatically indexing the clinical images based on a caregiver specialty, as an example. It is noted at the outset that the term "indexing" as used herein at least denotes the classification of image for use by particular caregivers, but may also include the processes of selecting a document type (e.g., "Annual Eye Exam"), selecting the particular patient encounter, selecting an index type (e.g., encounter, plan, or diagnosis), and adding comments and associated tags to the clinical image data.

Figure 1:
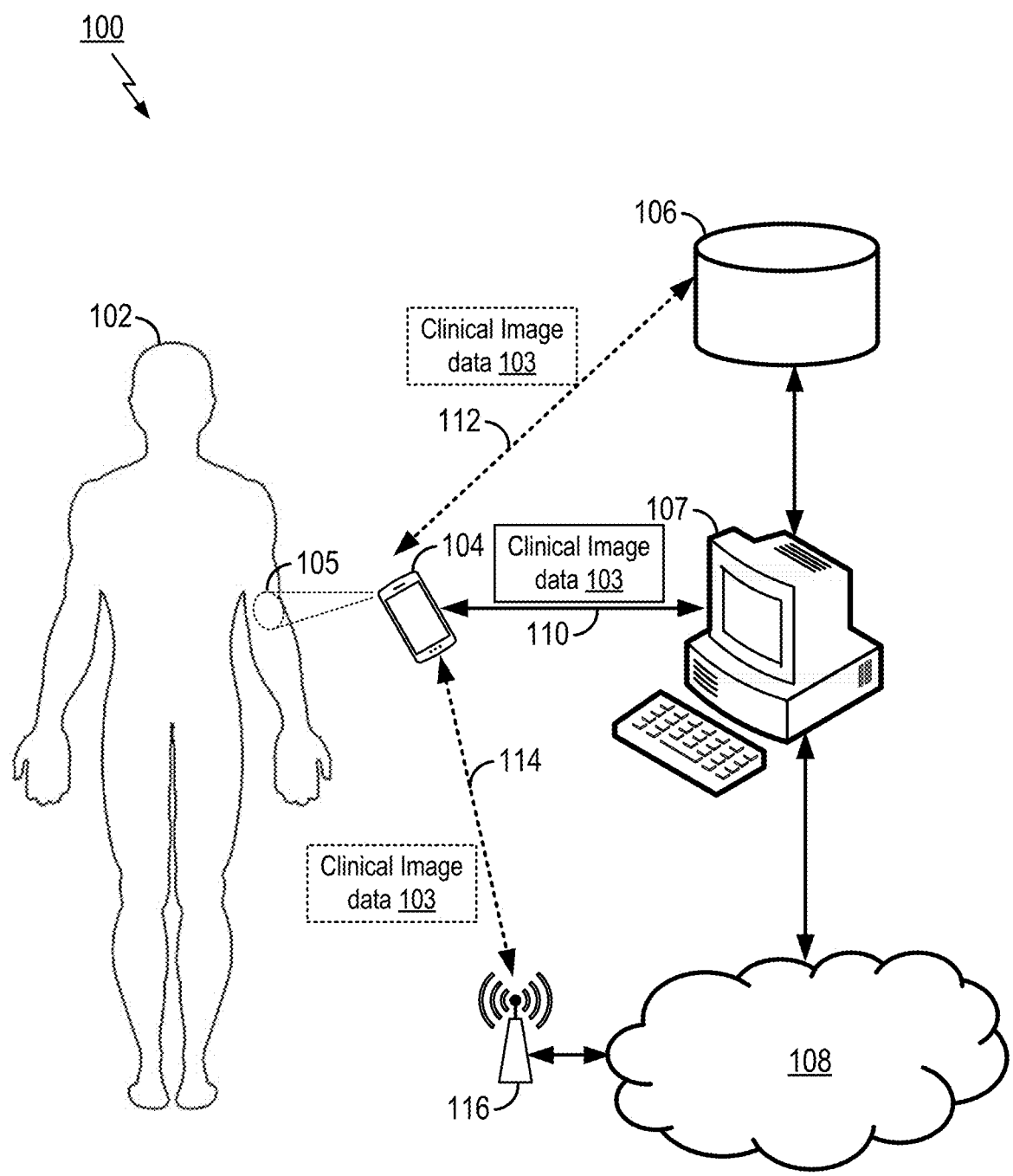
FIG. 1 illustrates an overview of a processor-based system including image capture devices, such as a portable device, and a processing apparatus communicatively coupled to a network under an illustrative embodiment.

Turning to FIG. 1, a system 100 is shown for collecting and processing (e.g., indexing) data including clinical images of a patient 102. In this example, clinical image data 103 may be obtained with mobile devices 104 used by caregivers at the point of service, such devices including a camera or photographic device. The camera device within mobile device 104 may be used to capture clinical images of relevant area of interest 105 of the patient 102. It is noted that while the mobile device 104 may consist of a wirelessly coupled mobile phone, tablet, or camera, the system 100 is not limited to use of such devices and any device, whether wireless or wired, that is capable of image capture may be utilized with the present systems, methods, or apparatus.

According to one aspect, clinical image data 103 obtained by the mobile device 104 may be transmitted to a database server 106, which is configured to store the clinical image data 103 via transmission and/or entry of the clinical image data 103 in a processing device 107 operatively coupled to the database server 106 with a communicative coupling 110, which may be wireless or wired. Alternatively, the clinical image data 103 may be obtained by the mobile device 104 and processed therein, and then transmitted to the database server 106 via a communicative coupling 112. Processing device 104 may also be operatively coupled to network 108, which may be configured as a local area network (LAN), wide area network (WAN), or any other suitable network. In yet other aspects, the mobile device 104 may be configured to communicate with other processing devices (not shown) within the network 108. In such case, the mobile device 104 may be configured to transmit clinical image data to the processing devices in the network 108 via a wireless access point 116 or similar means used to effectuate a local area network (LAN), including the use of technologies such as WiFi (IEEE 802.11) or Bluetooth, as examples.

It is noted that database 106 may be configured as a relational database or any other suitable database for processing data. In the embodiment of FIG. 1, database 106 is shown as a stand-alone database. However, those skilled in the art will appreciated that database 106 may be integrated into processing device 107, and/or located in the network 108. Database 106 may also be configured as part of a distributed database network, comprising a plurality of databases connected via network 108.

Figure 2:
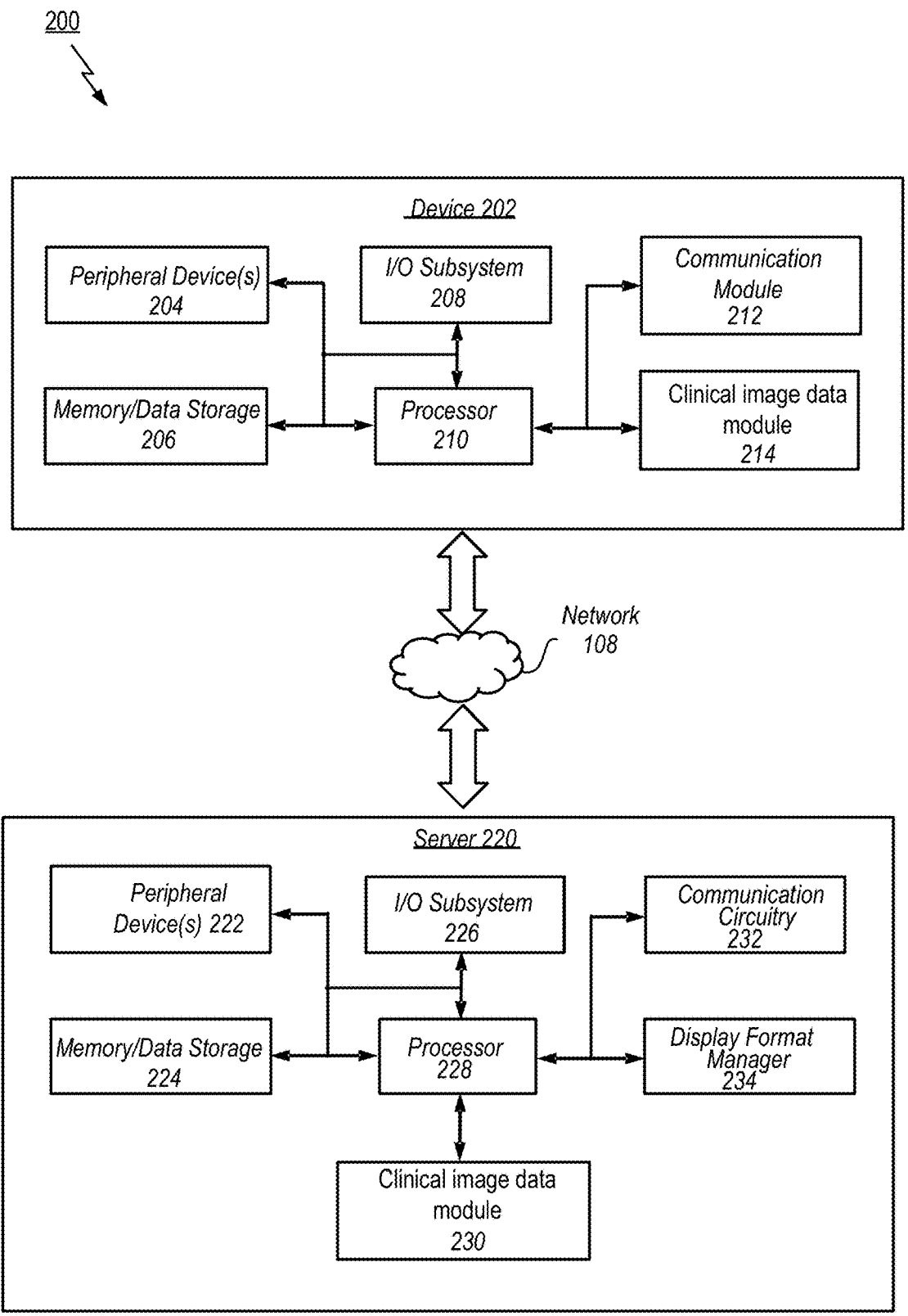
FIG. 2 schematically illustrates an operating environment for a portable device and a server communicatively coupled to a network for processing data under an illustrative embodiment.

FIG. 2 shows an operating environment for a system 200 that includes a processing device 202, which may be configured as device 104 including a peripheral camera device, and a server 220 communicating via the network 108, wherein the server 220 is configured to process clinical image data under an illustrative embodiment. In the illustrative embodiment, the processing device 202 includes a processor 210 or processor circuit, one or more peripheral devices 204, memory/data storage 206, communication circuity 212, and a clinical image data control module 214. Clinical image data control module 214 may be configured to process and/or manage clinical image data as will be described in greater detail below. The clinical image data control module 214 may be incorporated into memory/data storage 206 or may be a dedicated component, or incorporated into the processor 210. Processing device 202 may include other or additional components, such as those commonly found in a digital apparatus and/or computer (e.g., sensors, various input/output devices), in other embodiments. Additionally, in some aspects, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display interface, along with associated graphics circuitry and a touchscreen, a camera device for capturing clinical images, and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any type of server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated here for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. The server 220 also includes a network immunization data control module 230 that is configured to process sensor data for the clinical image data control module 214. The processing from network immunization data control module 230 may be configured as back-end processing, and/or may be configured to further process sensor data processed and/or pre-processed in clinical image data control module 214. Display format manager 234 is also operatively coupled to processor 228 and may be configured to format screens for device 202 based on data processed in the network immunization data control module 230. In some illustrative embodiments, network immunization data control module 230 and display format manager 234 may be integrated with clinical image data control module 214 to operate solely on device 202.

In the illustrated embodiment, communication between the server 220 and the processing device 202 takes place via the network 108 that may be operatively coupled to one or more network switches (not shown). In one embodiment, the network 108 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a radio access technology (e.g., GSM, LTE, Wideband Code Division Multiple Access (W-CDMA), etc.), and/or other communication protocols. As such, the network 108 may include any number of additional devices, such as additional computers, routers, and switches, to facilitate communications between the processing device 202 and the server 220.

Figure 3:
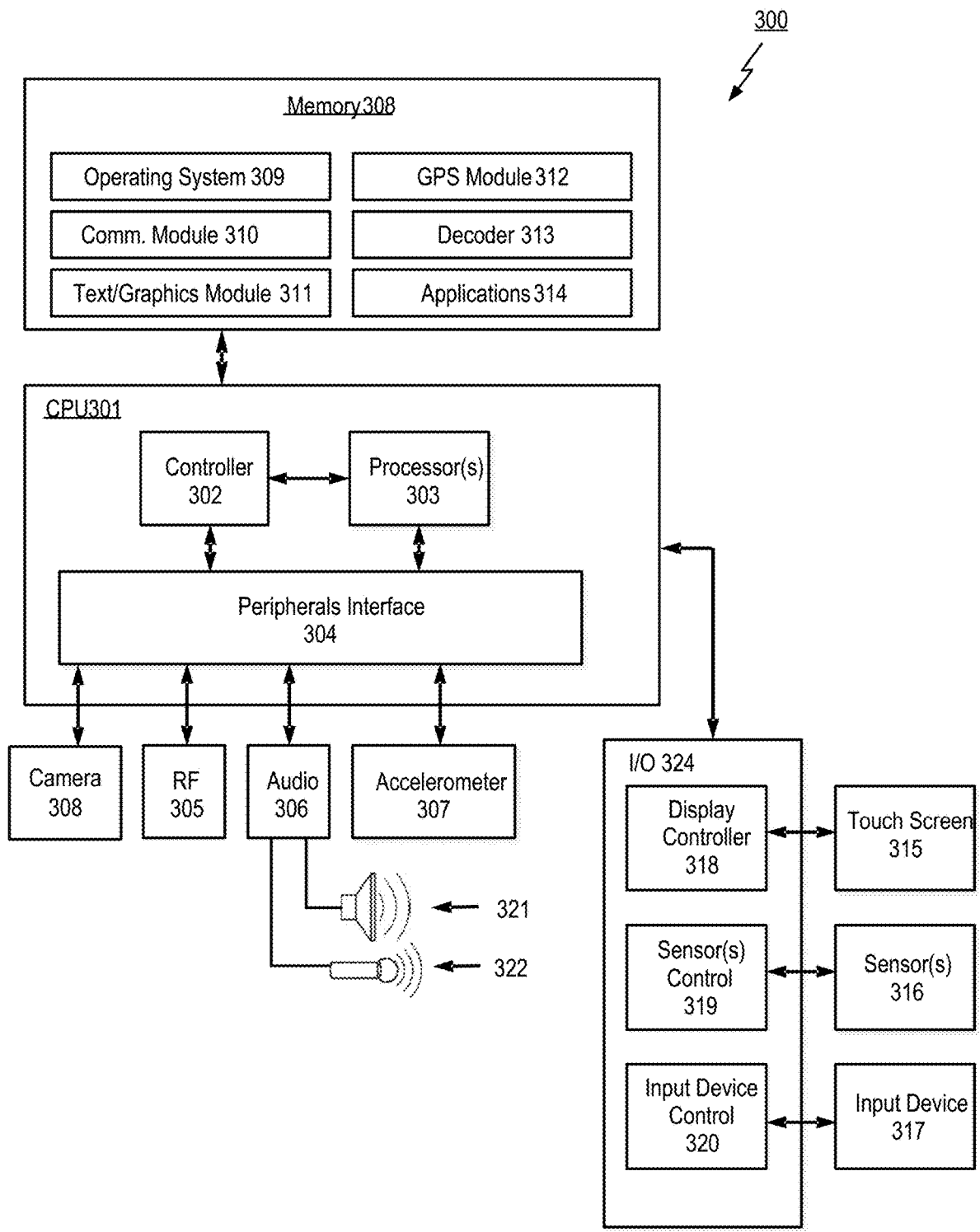
FIG. 3 schematically illustrates an operating environment for a portable device configured to process data under an illustrative embodiment.

FIG. 3 is an exemplary embodiment of a computing device 300 (such as processing device 104), and may be a personal computer, smart phone, tablet computer, laptop and the like. Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, camera 308, speaker 321, microphone 322, and input/output (I/O) subsystem 324 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), long term evolution (LTE), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both ears) and input (e.g., a microphone).

I/O subsystem 324 couples input/output peripherals on the device 300, such as touch screen 315, sensors 316 and other input/control devices 317, to the peripherals interface 304. The I/O subsystem 324 may include a display controller 318, sensor controllers 319, and one or more input controllers 320 for other input or control devices. The one or more input controllers 320 receive/send electrical signals from/to other input or control devices 317. The other input/control devices 317 may include electromechanical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/ to the touch screen 315. Touch screen 315 displays visual output to the user. The visual output may include graphics, text, icons, video, and any combination thereof. In some embodiments, some or all of the visual output may correspond to user-interface objects. Touch screen 315 may have a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In one embodiment, a point or contact between a touch screen 315 and the user corresponds to a finger of the user. Touch screen 315 may use LCD (liquid crystal display) technology, or LPD (light emitting polymer display) technology, although other display technologies may be used in other embodiments. Additionally, touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 such as heart rate sensors, touch sensors, as well as camera devices or optical sensors that comprise charge-coupled device (CCD) or complementary metal-oxide semiconductor (CMOS) phototransistors in some aspects, but not limited to such. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 324. The accelerometer is preferably configured to output accelerometer data in the x, y, and z axes for orientation sensing, as well as image stabilization when using the camera devices.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including health monitoring software, sensor software, navigation software, mapping, address books/contact list, email, instant messaging, and the like.

According to aspects of the present disclosure, the disclosed methods and apparatus afford improved speed and ease of indexing clinical images for electronic health record systems. In one aspect, the methods and apparatus disclosed herein may be used in the context of medical health record applications that are, in part, run on portable computer devices, such as device 104 in FIG. 1, device 202 in FIG. 2, or system 300 in FIG. 3. In particular, the present disclosure provides auto-indexing techniques that allow computer systems to more efficiently index and store clinical image data, which in turn allows system users to more quickly retrieve such data, as well as more efficiently associate the image data with other electronic records pertaining to patients and to specialists treating such patients.

Figure 4:
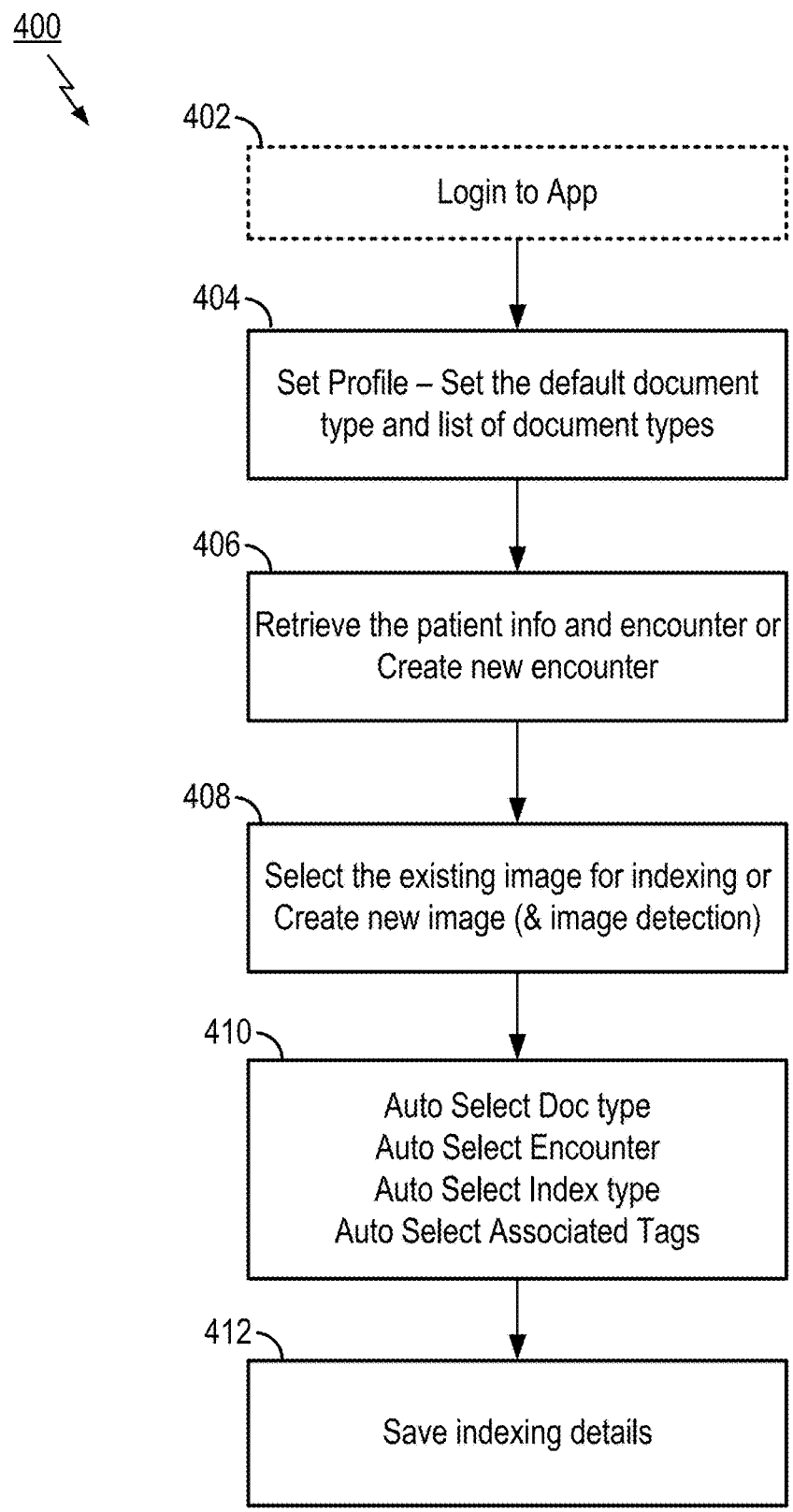
FIG. 4 illustrates a flowchart of an exemplary process for indexing clinical images.

FIG. 4 illustrates a flow diagram of an exemplary method 400 for providing auto-indexing of clinical images. While the method 400 is illustrated herein within the context of a particular health records computer system or application, it is noted that the clinical image indexing techniques disclosed herein are not limited to such and are applicable to other systems and applications.

As shown in FIG. 4, method 400 may include a first process 402 involving logging in to a particular application that includes the ability to capture/receive clinical images and index those images. After logging in, flow may proceed to a process 404 for setting a profile for a clinical images application that is used in indexing the clinical images after images are taken. This process 404 may involve selecting a document type (e.g., an annual eye exam), selecting an encounter, selecting an index type (e.g., the index type being one of a classification or identification that the data constitutes one of an encounter, a plan, and/or a diagnosis), and adding comments and associated tags, if necessary.

Figure 5:
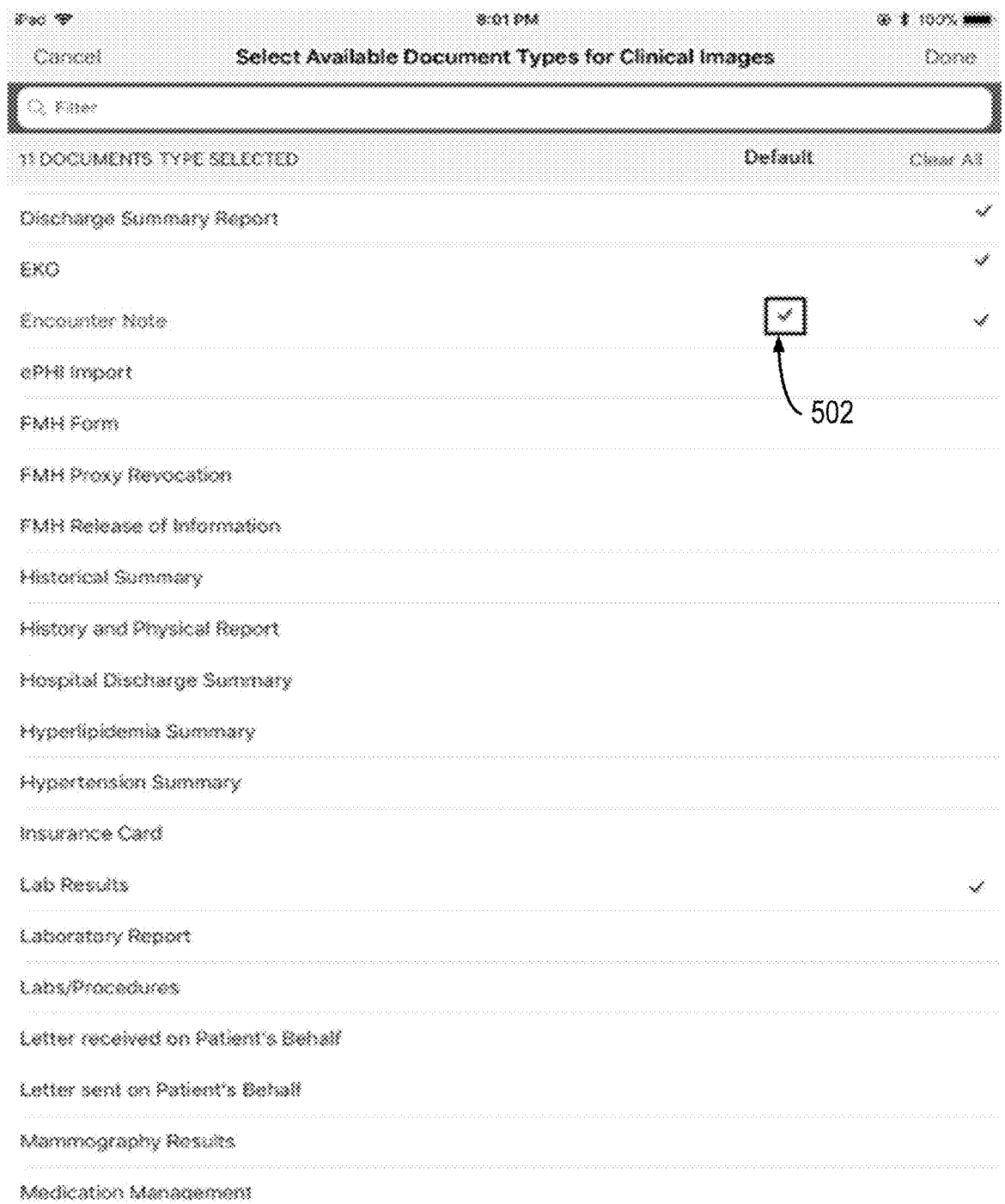
FIG. 5 shows an example of an interface that may be produced with an apparatus using the present methodology under an illustrative embodiment.

FIG. 5 shows an illustration of a user interface 500 used to select a document type for clinical images in accordance with the process 404 in FIG. 4. As may be seen in FIG. 4, various document types are selectable for respective types of clinical images. In the particular example illustrated in FIG. 5, the document type selected by the user is an encounter note, which would indicate that the type of image to be input to the electronic health record system will be from a patient encounter. In a similar manner, the system executing the application shown may be alerted for further processes of the clinical images types that will be selected, input, retrieved, or captured. In a further aspect, the application and interface may be configured to allow a user to select a default type of document as denoted by reference number 502

Figure 6:
FIG. 6 shows an example of an interface that may be produced with an apparatus using the present methodology under an illustrative embodiment.

Turning back to the method 400 of FIG. 4, flow proceeds from block 404 to block 406 where patient information is retrieved for the particular patient encounter. Alternatively, if the patient has not previously been treated by the care provider or user, a new encounter may be created. FIG. 6 illustrates an exemplary FIG. 600 of a user interface allowing a user to select the patient information at 602 (or, alternatively, create a new encounter, which is shown at 604 in FIG. 6). In further aspects, the process 406 may include accessing an appointment function that displays patient appointment information, wherein a user may select a particular patient appointment that precipitates or triggers the retrieval of the patient information.

Figure 7:
FIG. 7 shows an example of an interface that may be produced with an apparatus using the present methodology under an illustrative embodiment.

After process 406 is performed, method 400 in FIG. 4 proceeds to block 408 where either a clinical image is selected from a previously captured and stored image, or a new image is captured using a camera in a user device, such as device 104 in FIG. 1. An example of the user interface 700 displayed for this process 408 is illustrated in FIG. 7. As may be seen in FIG. 7, a captured clinical image 702 may be selected. In some aspects, the image 702 may be a previously captured and stored image that has been retrieved, such as when a particular patient's information is selected in the process of block 406, for example. In other aspects, the image 702 may be a presently captured image that has been captured in the environment of the application as illustrated by the capture image field 704. The captured clinical image may then be associated with the particular patient record that was selected.

In some aspects, method 400, and the processes of block 408 in particular, may further include image detection, image matching, or image registration that is performed on the captured clinical images to automatically detect human body shapes or parts. In this manner, the method 400 may then determine what anatomical features/parts to which the clinical image pertains. Additionally, method 400 may not only include detection of the particular human body parts to which an image is concerned, but also the image detection may be further utilize for the purposes of automatically indexing the images. For example, the process 400 may determine that an image of an eye would pertain to the eye, but also this detection may be further utilized to automatically index the image such as indexing that the clinical image relates to an eye appointment encounter or to a diagnosis of a condition of the eye.

Additionally, it is noted that the present methods and apparatus may employ any of a number of various processes for image detection. In one example, the image detection may involve comparing the captured image with pre-defined existing images of body shapes/parts. For example, in the case of an ear, nose, throat (ENT) specialist, a filter list of comparison images related to regions of ear, nose, throat, mouth, etc. could be defined. In this manner, each caregiver specialty may have some predefined filter list of comparison images which are compared against a captured clinical image for auto detection of the images. Examples of algorithmic mechanisms to detect and compare images may include key point image comparisons that detect by comparing the captured clinical image with the first 100 pixels, or a histogram method where the captured clinical image is compared with a predefined 3-color histogram (i.e., red, green, blue) with predefined two texture histograms. Other types of histogram methods that may be utilized may include a histogram intersection (HI) methods, merged palette histogram matching (MPHM) methods, or color ratio gradient (CRG) methods, as a few examples. According to other aspects of the present disclosure, it is contemplated that other image detection or registration technologies that may be utilized with the present methods and apparatus could include Speeded Up Robust Features (SURF), Scale Invariant Feature Transform (SIFT), Binary Robust Independent Elementary Features (BRIEF), Fast Retina Keypoint (FREAK), Oriented FAST and Rotated BRIEF (ORB), and/or Binary Robust Invariant Scalable Keypoints (BRISK), as a few examples.

Still further, it is noted that the present methods and apparatus may also employ deep neural networks (DNN) or deep learning algorithms for analyzing and detecting the clinical images, including image detection and determining type or classification. With regard to DNNs, any of a number architectures may be utilized, such as convolutional neural networks (CNNs) and recurrent neural networks (RNNs). It is further contemplated that DNNs usable in the present apparatus and systems may be configured to not only be utilized for image type recognition, such as which body part is being indexed, but also that object classification of parts of the clinical images may also be utilized. For example, if a patient has a lesion on the body part captured in the clinical image, the image recognition may include further recognition and classification of the image to include information of the particular condition, such as a lesion in this example.

Figure 8:
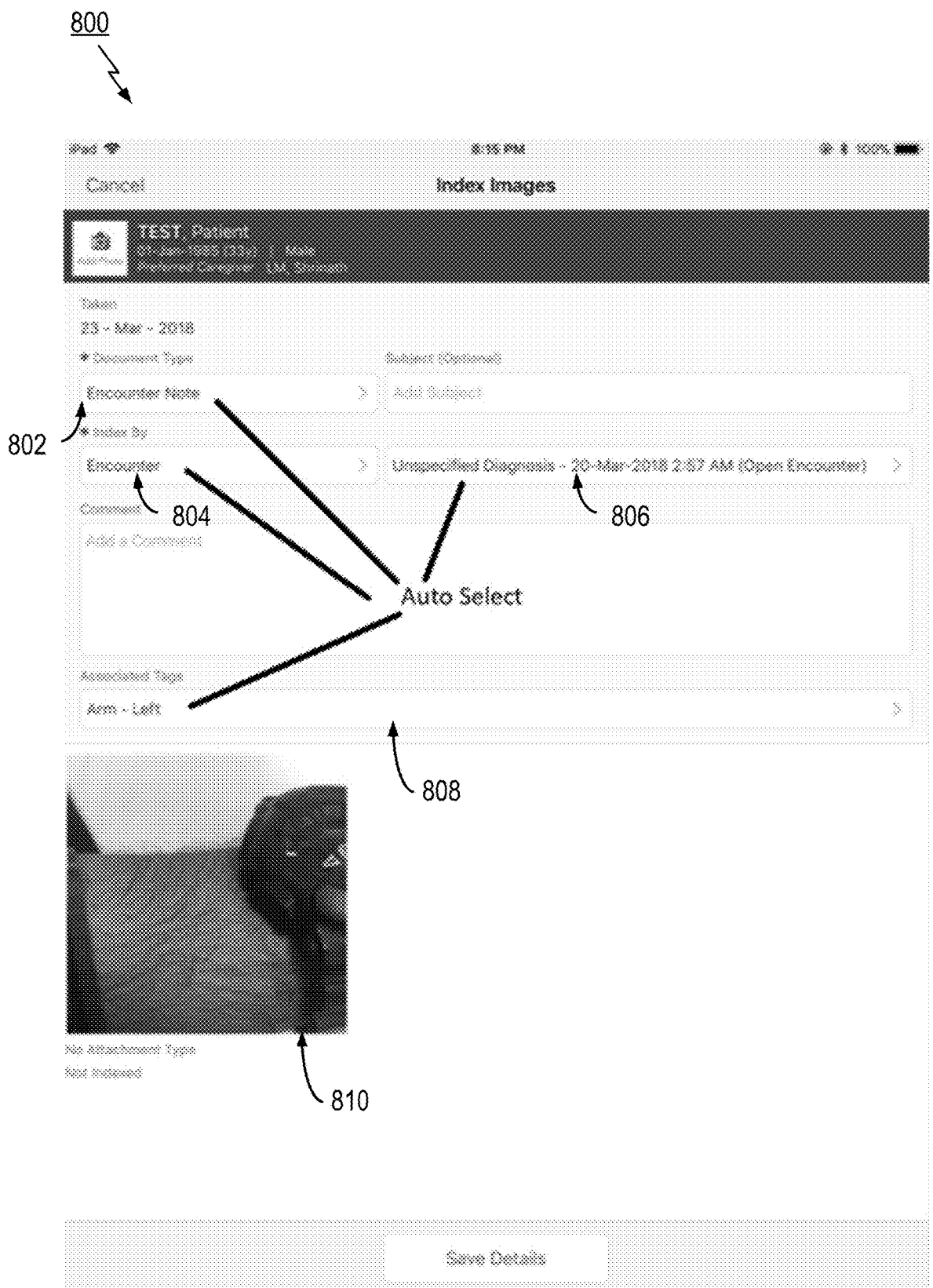
FIG. 8 shows an example of an interface that may be produced with an apparatus using the present methodology under an illustrative embodiment.

Turning back to FIG. 4, after the image capture and detection in process 408, flow proceeds to block 410 where the different automatic selection operations may be executed by a processing apparatus (e.g., one or both of devices 202 and 204 in FIG. 2 or 300 in FIG. 3), that is specifically configured to effectuate such automatic selection. In particular, the processes of block 410 may include one or more of an automatic selection of a document type, an encounter, an index type, and at least one associated tag. As an illustration, FIG. 8 shows an exemplary user interface 800 including a document type field 802, an index type field 804, an encounter field 806, and a tag field 808. Additionally, the particular retrieved or currently captured clinical image 810 pertinent to the various fields may also be displayed in the interface as shown in the example of FIG. 8.

With regard to the various automatically selected fields, the document type 802 may be selected based on the caregiver's or physician's specialty. In the example shown, the automatically selected document type would be an "encounter type" as one example, which may be predetermined through a default setting. It is noted that this auto selection would occur based on the default setting previously selected as shown at 502 in FIG. 5. In another example, for a specialty such as ophthalmology, a document type default for an ophthalmologist might be an "Annual Eye Exam", which would be auto selected based on the previously selected default. Thus, in general, the document type auto selection is performed in accordance with the default setting selected in the previously accessed profile setting screen or interface (See e.g., FIG. 5), and may be whatever document type is preferred based on physician preference or specialty. In other aspects, the present methodology is not limited to the selection of only one document type, and multiple document types may be selectable. In such case, dependent on the configuration of the user interface and what information is desired to displayed to a user, a dominant or prioritized default document type may be auto selected and displayed among the multiple default document types. Alternatively, in other aspects the multiple default document types may be simultaneously auto selected and displayed in the interface.

With regard to the automatic selection of the encounter field 806, it is noted that the processing apparatus may be configured such that whenever a clinical image is taken, the default automatic selection for this field may be configured such that an open encounter is indicated as presently occurring as illustrated in the example of FIG. 8. Those skilled in the art will appreciate that this automatic selection is merely exemplary, and other encounter field selections capable of being auto selected may be contemplated.

Figure 9:
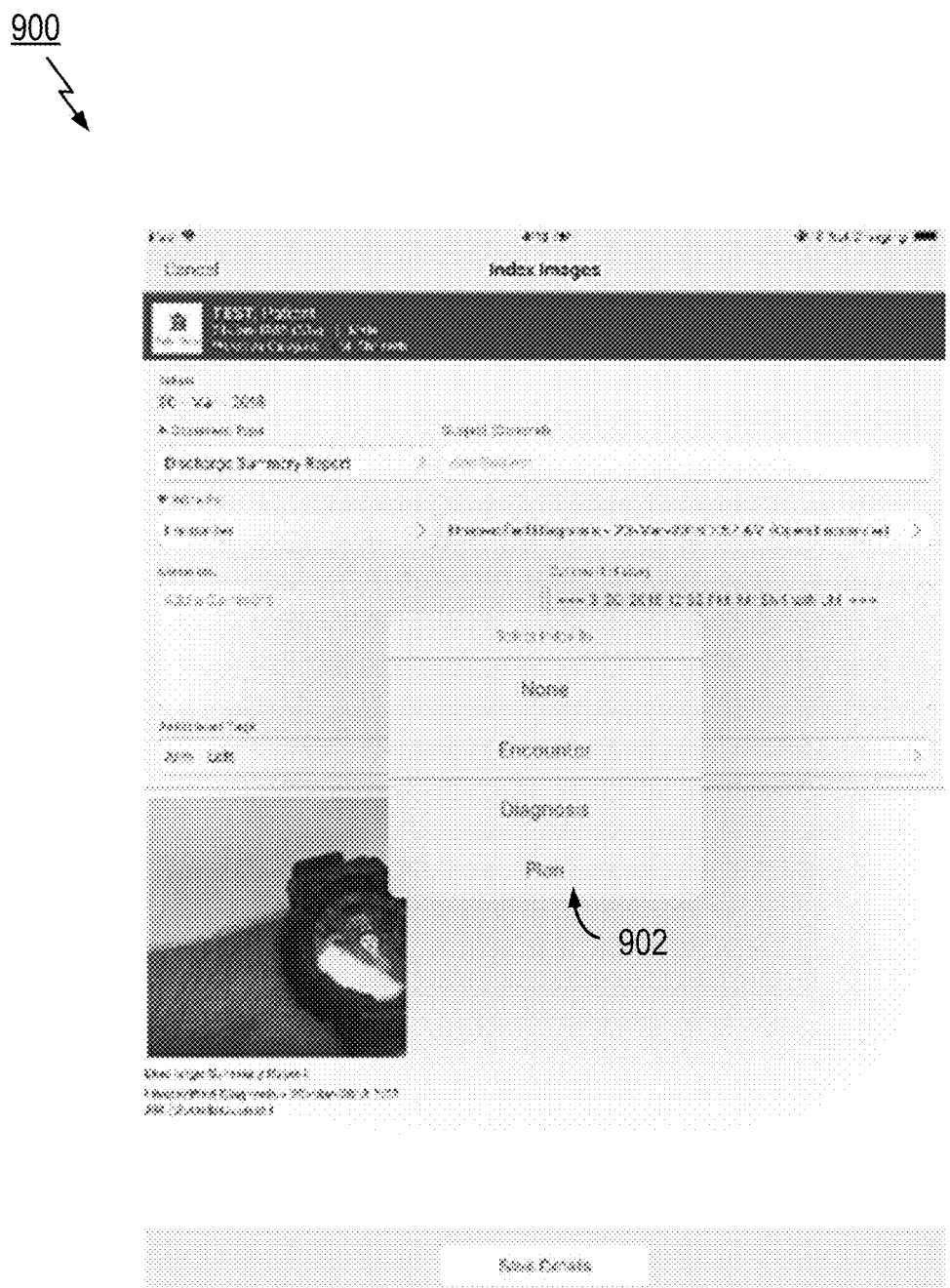
FIG. 9 shows an example of an interface that may be produced with an apparatus using the present methodology under an illustrative embodiment.

Concerning the index type selection (i.e., field 804), in an aspect, the index type may be automatically selected among three types of indexing: encounter, plan, or diagnosis. In a particular aspect, it is noted that if the automatic selection of encounter field is set at a default of "encounter" or "create new encounter," the index type may be configured to auto select the index type "encounter" as shown in the example of FIG. 8, but the method is not limited to such. Furthermore, the processing apparatus may be configured to allow editing of the index field prior to saving the index that will be associated with the clinical image. As an example, FIG. 9 illustrates a user interface 900 that may be displayed during process 410 such as through a tap or click on the field 804, which provides an editing selection 902 that affords a user the ability to manually select among the three exemplary index types. While the presently described methods and apparatus provide selection among three distinct index types, it will be appreciated by those skilled in the art that other index types and numbers thereof may be contemplated and accommodated.

Figure 10:
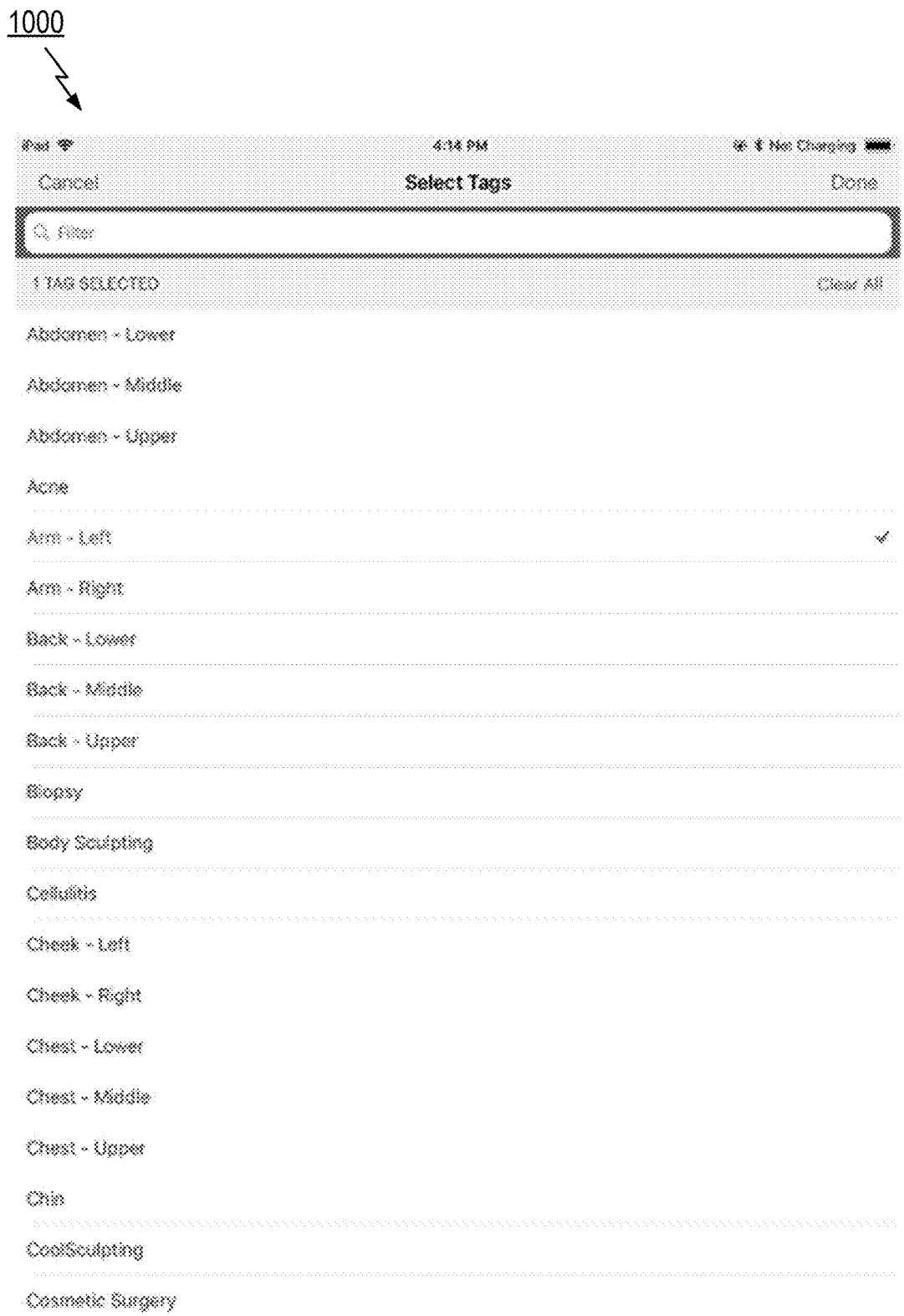
FIG. 10 shows an example of an interface that may be produced with an apparatus using the present methodology under an illustrative embodiment.

With respect to the automatically selected associate tag as shown at field 808 in FIG. 8, it is noted that this automatic selection may be based on the image recognition. For example, if an image a patient's left arm is captured and the image is recognized as such through the image recognition processes, the tag field 808 will be populated with a tag such as "Arm-Left", for example. In further aspects, it is noted that the system may include a number of predefined tags that could be selected manually, which can be single or multiple selected while indexing. An example of such a selection of tags is illustrated in FIG. 10 showing a display screen 1000 featuring various tags.

After the automatic selection processes of block 410 are completed, flow proceeds to block 412 where, among other things, the indexing details are saved, along with the clinical image data in the case of a current image capture.

In other aspects, it is noted that the system (e.g., system 100) may be configured to automatically network devices for image capture such as device 104 with local area networks such as with wireless WiFi or Bluetooth networks, within a particular area (e.g. a hospital). According to one example, networked devices may be communicatively couplable with various access point (AP) devices (e.g., multiple APs 116 as illustrated in FIG. 1) in a particular facility or area so that the image capture and indexing method may be operable for accessing and storing images that may be stored outside of a device, such as in a database (e.g., 106), as well as access wide area networks as well (e.g., Internet). As the device (e.g., device 104) is moved throughout the facility, the device may either push and/or pull data including clinical image data and associated index/encounter/tag data, patient data. In further aspects, data concerning the location of the device within a facility may be determined to identify a room, medical service (radiology, surgery, orthopedics, ophthalmology, cardiology, oncology, etc.), the attending doctor, patients, and so forth. Thus, in further aspects, location data may be used to automatically determine index and encounter fields, and even auto select a particular patient's data for processes discussed above. Yet further, as the device is moved to a different location, the system may be configured to utilize location data to dynamically update particular fields. Thus, for example, if clinical images for a patient record are captured in the surgery department and then the patient is subsequently moved to a recovery room, the location data may be utilized such that the clinical image taken in surgery has associated encounter data and indices that are automatically selected, whereas the clinical images captured in recovery may have different auto selected fields based on the detection of being located in another room (e.g., the recovery room).

Furthermore, in other aspects, the processing methods and apparatus may be configured to store the clinical images at varying levels of image resolution. For example, in instances where the specialty and the nature of the images relating to the specialty do not require fine image resolution, the image resolution may be reduced to save memory space and the need for more complex or higher level image compression. Still further, it is noted that the system may be configured to compare two different clinical images taken at different times for evaluation of a plan of treatment or for differential diagnosis. In such case, the automatic indexing could be configured to default to indices such as "plan" or "diagnosis" where appropriate.

Of further note, FIGS. 5-10 show examples of interfaces that may be produced under the present disclosure. It is to be understood by those skilled in the art that the screen panels or displays may be combined in various ways, or may be subjected to minification to provide efficient rendering of the panels. Also, depending on the processing described above, various warnings/alerts (810) may be provided to allow a health care provider to take the necessary actions or to retake photographs.

Figure 11:
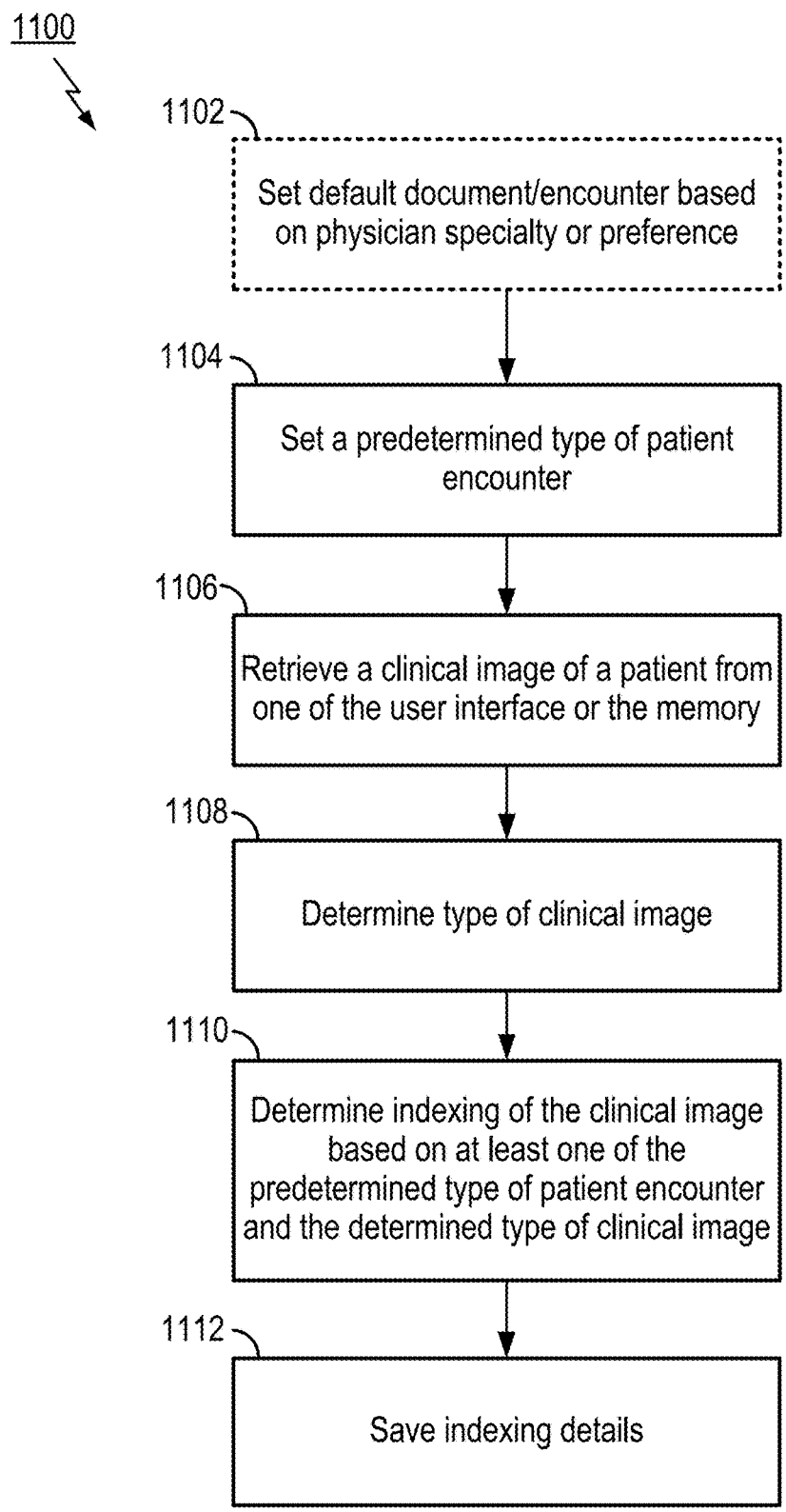
FIG. 11 illustrates a flowchart of another exemplary method for indexing clinical image under an illustrative embodiment.

FIG. 11 illustrates a flowchart of another exemplary method 1100 for managing clinical images in an electronic health record system. It is noted that method 1100 may be a processor based method and further may be executed by one or more of devices 104, 106, 107, and 108 in FIG. 1, devices 202 and 220 in FIG. 2, or 300 in FIG. 3. As illustrated, method 1100 may include setting a default physician specialty or preference as shown at block 1102. Method 1100 further includes setting a predetermined type of patient encounter as shown in block 1104. Furthermore, method 1100 includes retrieving a clinical image of a patient from one of the user interface or the memory as shown at block 1106. Yet further, method 1100 includes determining determine a type of the clinical image as shown at block 1108, which may further include determining the type by performing the image recognition as discussed before. Additionally, method 1100 may include indexing of the clinical image based on at least one of the predetermined type of patient encounter and the determined type of clinical image as shown in block 1110. Finally, method 1100 may include saving the indexing details as illustrated at block 1112.

In light of foregoing disclosure, those skilled in the art will appreciate that the present methods, systems, and apparatus afford physicians or caregivers, through automatic or automated indexing of clinical images, image auto detection, auto detection and selection of associated tags, auto setting document types, auto selection of an encounter, and/or automatic selection of an index type, a reduction in the time of the workflow indexing the clinical images. This time savings reduces the time needed to document the patient records, allowing physicians and caregivers to concentrate more time with a patient.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A processor-based method for automatically indexing and managing clinical images in a medical processing system of a computer network, comprising:
    receiving a clinical image of a patient from one of a user interface or memory of the medical processing system, wherein the clinical image comprises updatable location data associated with the clinical image, the location data indicating a location within a medical facility in which the clinical image was taken;
    processing, via a processor, the clinical image to determine a type of clinical image utilizing at least one of key point image comparison and a histogram comparison;
    automatically populating, via the processor, at least a portion of a tag field for the clinical image based on the determined type and location data, wherein the tag field comprises information showing characteristics of the clinical image and location;
    receiving data indicating a type of patient encounter associated with the clinical image; and
    generating, via the processor, an indexed clinical image for the medical processing system, wherein the indexed clinical image is configured to indicate the type of clinical image, the automatically populated tag field, and patient encounter type, wherein the indexed clinical image is further configured to be pushed to, or pulled by access point devices communicating with the medical processing system, based at least in part on the indexing and updatable location data.

2. The processor-based method of claim 1, wherein processing the clinical image and automatically populating at least a portion of the tag field comprises applying a deep neural network to the clinical image.

3. The processor-based method of claim 1, wherein the determined indexing includes determining indexing for the clinical image with an index comprising an index indicating one of:
    an encounter of a physician with a patient;
    a plan of patient treatment; and
    a diagnosis of a patient condition.

4. The processor-based method of claim 1, further comprising automatically selecting, via the processor, for the indexed clinical image:
    a document type based on the set default physician preference or specialty;
    a patient encounter type based on at least one of the set default physician preference or specialty and the clinical image; and
    further associated tag information based on the clinical image.

5. A system for automatically indexing and managing clinical images in a computer network, the system comprising:
    a processing apparatus;
    a memory operatively coupled to the processing apparatus, the memory configured to store clinical images; and
    a user interface;
    wherein the processing apparatus is configured to:
        receive a clinical image of a patient from one of a user interface or memory of the processing system, wherein the clinical image comprises location data associated with the clinical image, the location data indicating a location within a medical facility in which the clinical image was taken;
        process the clinical image to determine a type of clinical image utilizing at least one of key point image comparison and a histogram comparison;
        automatically populate at least a portion of a tag field for the clinical image based on the determined type and location data, wherein the tag field comprises information showing characteristics of the clinical image and location;
        receive data indicating a type of patient encounter associated with the clinical image; and;
        generate an indexed clinical image for the medical processing system, wherein the indexed clinical image is configured to indicate the type of clinical image, the automatically populated tag field, and patient encounter type, wherein the indexed clinical image is further configured to be pushed to, or pulled by access point devices communicating with the medical processing system, based at least in part on the indexing and updatable location data.

6. The system of claim 5, wherein the processing apparatus is configured to process the clinical image and automatically populating at least a portion of the tag field by applying a deep neural network to the clinical image.

7. The system of claim 5, wherein the determined indexing includes determining indexing for the clinical image with an index comprising an index indicating one of:
    an encounter of a physician with a patient;
    a plan of patient treatment; and
    a diagnosis of a patient condition.

8. The system of claim 5, wherein the processing apparatus is configured to automatically select, for the indexed clinical image:
    a document type based on the set default physician preference or specialty;
    a patient encounter type based on at least one of the set default physician preference or specialty and the clinical image; and
    further associated tag information based on the clinical image.

\* \* \* \* \*